(12) United States Patent
Cabeza-Guillen et al.

(10) Patent No.: US 10,890,786 B2
(45) Date of Patent: Jan. 12, 2021

(54) METHOD AND SYSTEM FOR DETERMINING AN ADAPTIVE PARAMETER FOR A SPECTACLE LENS ACCOMMODATED IN A SPECTACLE FRAME

(71) Applicant: Carl Zeiss Vision International GmbH, Aalen (DE)

(72) Inventors: Jesus-Miguel Cabeza-Guillen, Aalen (DE); Subhashini Mani, Aalen (DE); Michael Gamperling, Leipheim (DE)

(73) Assignee: Carl Zeiss Vision International GmbH, Aalen (DE)

(*) Notice: Subject to any disclaimer, the term of this patent is extended or adjusted under 35 U.S.C. 154(b) by 300 days.

(21) Appl. No.: 15/212,060

(22) Filed: Jul. 15, 2016

(65) Prior Publication Data

US 2016/0357032 A1    Dec. 8, 2016

Related U.S. Application Data

(63) Continuation of application No. PCT/EP2015/050554, filed on Jan. 14, 2015.

(30) Foreign Application Priority Data

Jan. 15, 2014  (DE) .................... 10 2014 200 637

(51) Int. Cl.
*G02C 13/00* (2006.01)
*A61B 3/00* (2006.01)
*A61B 3/11* (2006.01)

(52) U.S. Cl.
CPC .......... *G02C 13/005* (2013.01); *A61B 3/0025* (2013.01); *A61B 3/111* (2013.01)

(58) Field of Classification Search
USPC ..... 351/204, 246, 200, 206; 348/E7.018, 78; 382/117
See application file for complete search history.

(56) References Cited

U.S. PATENT DOCUMENTS

| | | |
|---|---|---|
| 6,659,609 B2 | 12/2003 | Mothes |
| 7,588,335 B2 | 9/2009 | Kubitza |
| 7,950,800 B2 | 5/2011 | Nauche et al. |
| 2009/0214086 A1 | 8/2009 | Thomet |
| 2010/0128220 A1 | 5/2010 | Chauveau |

(Continued)

OTHER PUBLICATIONS

International Search Report dated May 4, 2015 of international application PCT/EP2015/050554 on which this application is based.

(Continued)

*Primary Examiner* — James C. Jones
(74) *Attorney, Agent, or Firm* — Walter Ottesen, P.A.

(57) ABSTRACT

In a method for determining at least one fitting parameter for a spectacle lens received in a spectacle frame, an image, lying in an image plane, of at least one portion of a spectacle frame worn by a subject is acquired. When acquiring the image, the inclination of the image plane about a horizontal axis which is parallel to the image plane is established and, in the process, the at least one fitting parameter is established from the acquired image of the portion of the subject with the spectacle frame worn by the subject and the established inclination of the image.

11 Claims, 4 Drawing Sheets

(56) References Cited

U.S. PATENT DOCUMENTS

| | | | |
|---|---|---|---|
| 2010/0195045 A1* | 8/2010 | Nauche | G02C 13/005 351/204 |
| 2013/0188128 A1 | 7/2013 | Divo et al. | |
| 2014/0240664 A1 | 8/2014 | Divo et al. | |

OTHER PUBLICATIONS

DIN EN ISO 13666: 2012 of the Din Deutschen Institut fuer Normung, e.V., Oct. 2013, pp. 1 to 110 (114 pages).
International Preliminary Report on Patentability and Written Opinion dated Oct. 10, 2019 of corresponding international application PCT/EP2015/050554.

* cited by examiner

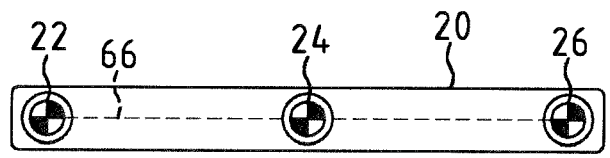
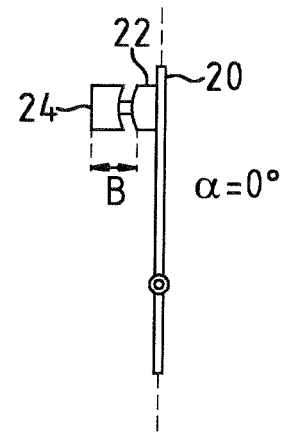
FIG. 3A
FIG. 3B
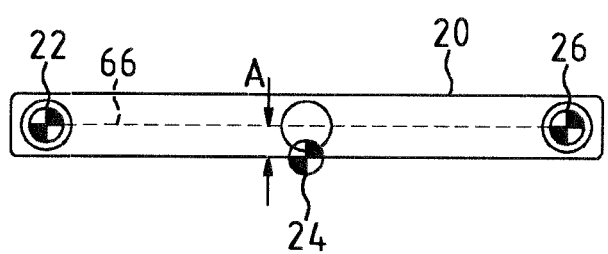
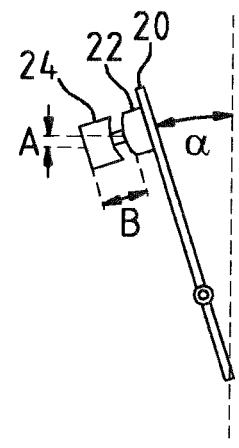
FIG. 4A
FIG. 4B
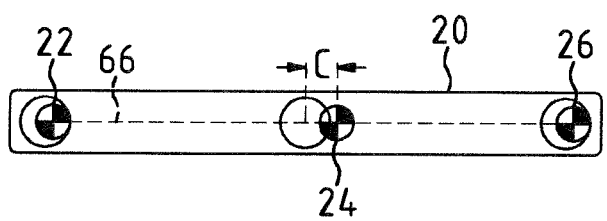
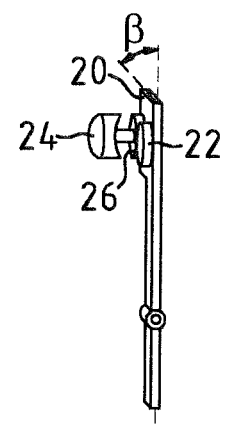
FIG. 5A
FIG. 5B

METHOD AND SYSTEM FOR DETERMINING AN ADAPTIVE PARAMETER FOR A SPECTACLE LENS ACCOMMODATED IN A SPECTACLE FRAME

CROSS REFERENCE TO RELATED APPLICATIONS

This application is a continuation application of international patent application PCT/EP2015/050554, filed Jan. 14, 2015, designating the United States and claiming priority from German application 10 2014 200 637.6, filed Jan. 15, 2014, and the entire content of both applications is incorporated herein by reference.

FIELD OF THE INVENTION

The invention relates to a method for determining at least one fitting parameter for a spectacle lens which is to be received in a spectacle frame. In the method, an image, lying in an image plane, of at least one portion of a spectacle frame worn by a subject is acquired. Moreover, the invention also relates to a system for determining such a fitting parameter and to a computer program.

BACKGROUND OF THE INVENTION

In order to fit the spectacle lenses correctly into a spectacle frame, it is necessary to determine so-called fitting parameters so that the optical centers of the lenses can be made to coincide with the visual axes of the corresponding eyes in order thus, for example, to know information about the interpupillary distance and the information about the elevation of the pupils in relation to the spectacle frame.

Moreover, it is likewise important to determine the elevation of the optical centers of the spectacle lenses in relation to the upper or lower edge of the spectacle frame, into which the spectacle lenses are inserted.

By way of example, fitting parameters can be determined by virtue of an optician and a subject sitting or standing opposite one another. The subject seats the frame of his choice in place with a glass lens held therein. The subject is asked to look into the distance and the optician then indicates the visual point with a cross on the lens or on a contact line foil according to appearance, as identified when looking at one another. This cross (centering cross) then determines the position of the optical center of the spectacle lens to be inserted into the frame. This method is carried out individually for each eye of a subject. The distance between the centering crosses established in this manner is the interpupillary distance PD.

WO 01/84222 A1 describes a system for determining fitting parameters for spectacle lenses which contains a digital video camera accommodated on a column in a height-adjustable manner. The lens of the video camera is arranged in the region of the front surface of the housing, together with a mirror and a light source. This system includes a computer connected to the digital video camera. The computer determines fitting parameters for the spectacle frame by image evaluation from the image of a spectacles wearer with a spectacles frame and a measurement bracket fastened to the spectacles frame.

SUMMARY OF THE INVENTION

It is an object of the invention to enable the determination of different fitting parameters for spectacle lenses in a spectacle frame with less complexity.

The invention is based on the idea that, in order to determine the fitting parameters for spectacle lenses in a spectacle frame by analyzing images of a spectacle frame, provided with a measurement bracket seated on a subject, it is not absolutely necessary to use a camera securely installed in the room but that these fitting parameters can, in principle, also be determined by virtue of images taken by a hand-held camera which, for example, is integrated into a tablet computer being evaluated. However, the inventors have recognized that the fitting parameters determined in this way often deviate from the fitting parameters which are determined by analyzing corresponding images which are acquired by a camera securely installed in the room, as is described, for example, in WO 01/8422 A1.

In comprehensive trials, the inventors found out that the inclination angle of the image plane of the camera in relation to the vertical direction when recording the images is decisive for the error which may occur when determining spectacle lens fitting parameters for spectacle lenses, which should be accommodated in a spectacle frame, by analyzing images of the spectacle lens put on by a subject if the corresponding images are recorded by a camera which is not securely installed but is held in the hands.

In particular, the inventors found out that the influence of the inclination angle of the image plane of the camera in relation to the vertical direction cannot be readily compensated by means of image evaluation, unlike the tilt of the camera about the optical axis of a camera lens system or the swiveling of the camera about an axis extending in the vertical direction.

Thus, an idea of the invention is, in particular, to acquire the inclination of the camera image plane in relation to the vertical direction by means of an inclination sensor, as is routinely integrated in tablet computers with a camera, such as, for example, the iPad®, or in smartphones with a camera, such as, for example, the iPhone®, and then to take this into account when determining the fitting parameters for spectacle lenses by image evaluation of images of a spectacle frame which is provided with a measurement bracket and put on by a subject.

That is to say, if, for example, a tablet computer is not held precisely vertically during the recording, the pantoscopic angle for spectacle lenses in the spectacle frame, as observed by the camera, deviates from the actual pantoscopic angle of these spectacle lenses, and so very large errors may occur, for example, when calculating centration data by means of image evaluation from such recordings.

Therefore, in order to determine at least one fitting parameter for a spectacle lens received in a spectacle frame, the invention proposes to acquire an image, lying in an image plane, of at least one portion of a spectacle frame which is worn by the subject, wherein the inclination of the image plane about a horizontal axis parallel to the image plane is also established when acquiring the image in order, then, to calculate the at least one fitting parameter from the acquired image of the portion of the subject with the spectacle frame worn by the subject by means of image evaluation, taking into account the established inclination of the image.

Preferably, to this end, the image of the spectacle frame is acquired by a digital camera containing an inclination sensor acquiring the inclination of the image plane about a horizontal axis.

By way of example, this inclination sensor can be a gravity sensor which establishes the direction of gravity. As an alternative thereto, the inclination sensor can also be embodied as a sensor which evaluates the direction of the Earth's magnetic field. In particular, the inclination sensor can also be a sensor evaluating both the direction of the Earth's magnetic field and the direction of gravity (combined gravity/magnetic field sensor).

Here, the image of the portion of the spectacle frame worn by the subject can be acquired, for example, if a measurement bracket is connected to the spectacle frame, said measurement bracket having a front side with at least three front target marks for measuring the pantoscopic angle ($\alpha$) of the spectacle frame to be measured, wherein at least one of the front target marks is arranged spatially offset perpendicular to the front side of the measurement bracket in relation to the at least two other front target marks.

According to the invention, a pantoscopic angle is established from the image by means of image analysis, said pantoscopic angle being corrected in accordance with the detected inclination of the image plane. Preferably, a head rotation angle $\beta$ related to the optical axis of the camera is also established from the image by means of image analysis, said head rotation angle, where possible, likewise being corrected in accordance with the detected inclination of the image plane. Here, the head rotation angle $\beta$ is understood to be the angle which the optical axis of the camera forms with a plane which is perpendicular to the distance line of the pupils of the eyes of the subject.

Thus, it is possible, for example, to determine, as fitting parameter, the frame dimensions (l, h, AzG [distance between lenses]), the interpupillary distance (PD, $z_R$, $z_L$), the centration distance ($x_R$, $y_R$, $x_L$, $y_L$), the vertex distance (HSA), the pantoscopic tilt, the face form angle and/or the required lens blank diameter.

A system according to the invention for determining at least one fitting parameter for a spectacle lens received in a spectacle frame contains a camera, which has an image plane, an inclination sensor acquiring the inclination of the image plane of the camera about a horizontal axis and a computer unit. This computer unit contains a computer program which, according to the method described above, establishes the at least one fitting parameter for a spectacle lens received in a spectacle frame from an image, acquired by the camera, of a portion of a spectacle frame worn by a subject and the established inclination of the image.

The camera can be integrated into a tablet computer and/or a cellular telephone, wherein the computer unit is preferably embodied as a server connected to the tablet computer and/or the cellular telephone. In this way it is possible to ensure a short computational time for evaluating the acquired images.

By virtue of the tablet computer and/or the cellular telephone communicating wirelessly with the server, it is possible to record the images of a portion of a spectacle frame worn by a subject with the greatest possible freedom of movement.

The computer program according to the invention contains program code for carrying out the steps of the above-described method when the computer program is executed in the computer unit of a system according to the invention.

BRIEF DESCRIPTION OF THE DRAWINGS

The invention will now be described with reference to the drawings wherein:

FIG. 3A and FIG. 3B show views of front target marks of the measurement bracket in the case of a spectacle frame without pantoscopic tilt;

FIG. 4A and FIG. 4B show views of front target marks of the measurement bracket in the case of spectacle frame with pantoscopic tilt;

FIG. 5A and FIG. 5B show views of front target marks of the measurement bracket for a head position of the subject, in which he does not look into the camera;

DESCRIPTION OF THE PREFERRED
EMBODIMENTS OF THE INVENTION

Figure 1:
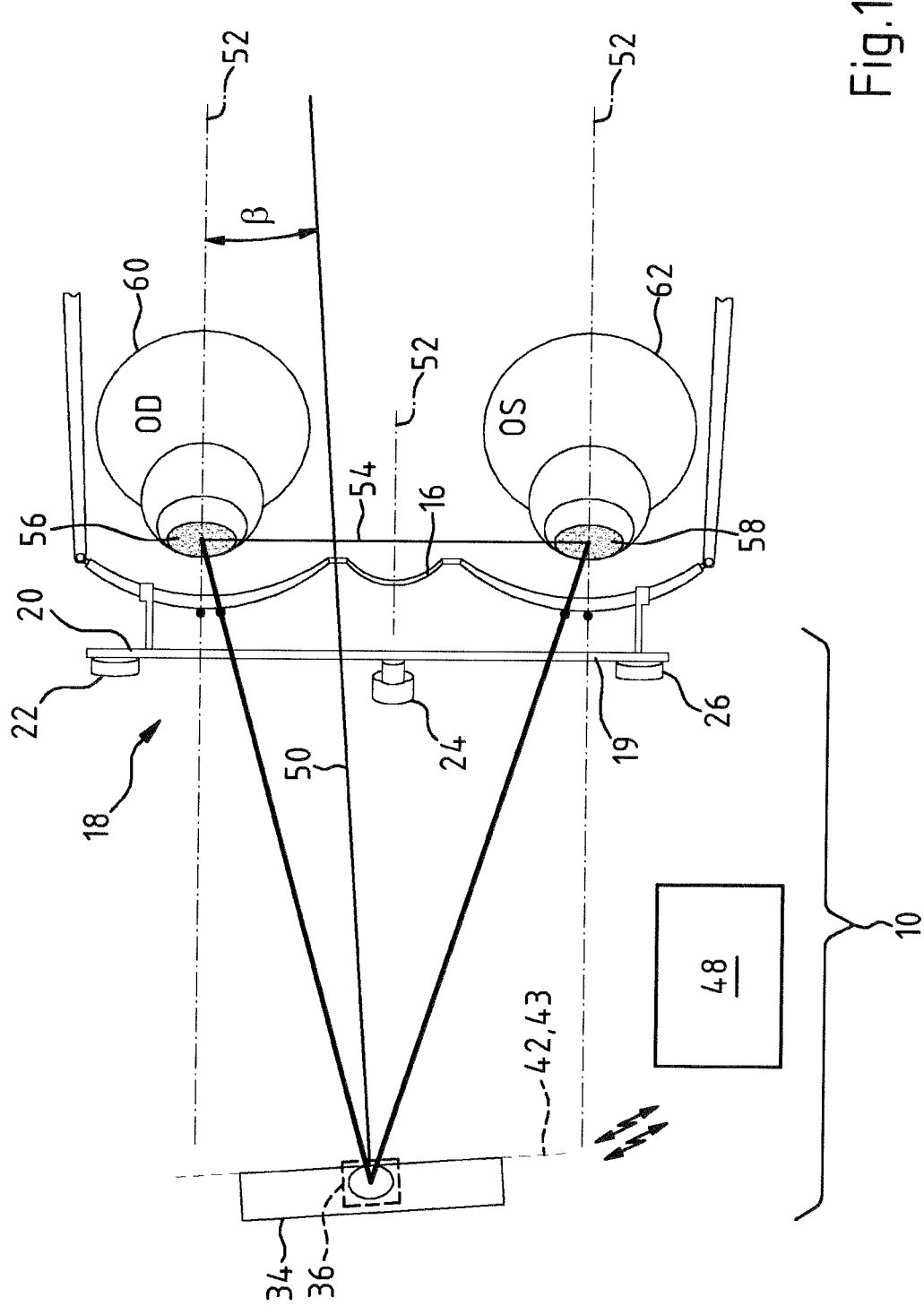
FIG. 1 shows a system for determining fitting parameters for a spectacle lens received in a spectacle frame with a measurement bracket and with a camera, in a view from above.

The system 10 shown in FIG. 1 allows a user to determine fitting parameters for a first spectacle lens 12 and a second spectacle lens 14, which are intended to be held in a spectacle frame 16 already adapted to the anatomy of a spectacle wearer. To this end, the system 10 contains a measurement bracket 18, which can be detachably fastened to the spectacle frame 16. By way of example, the measurement frame 18 can have the setup as described in U.S. Pat. No. 7,588,335, the entirety of which is referred to in this respect and the disclosure of which is herewith completely incorporated into the description of the invention.

For the purposes of fitting to different frame geometries, the measurement bracket 18 has an adjustable traverse 20 and two adjustable limbs (not depicted here) which are mounted with pivotable movement. Using this, the measurement bracket 18 can be clamped to a spectacle frame 16 by means of frame receptacles arranged on the traverse 20 and the adjustable limbs.

At the front side 19 thereof, the measurement bracket 18 is provided with a left, a central and a right front target mark 22, 24, 26. The front target marks 22, 24, 26 are arranged in the region of the traverse 20. Here, the left and right front target marks 22, 26 are positioned in a manner recessed in relation to the central front target mark 24.

Figure 2:
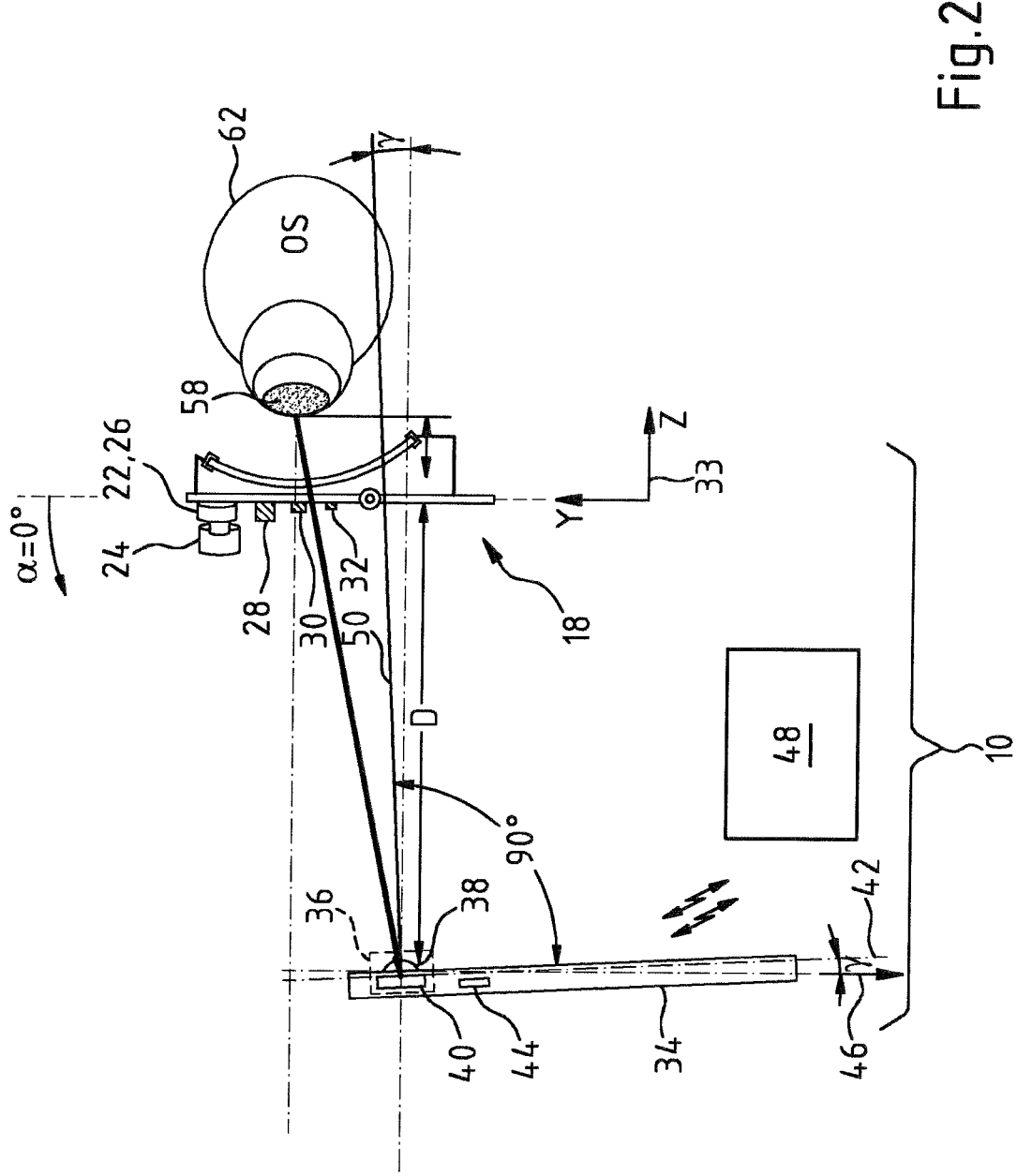
FIG. 2 shows the system for determining fitting parameters in a side view.

FIG. 2 is a side view of the system 10. In each case, the measurement bracket 18 has three side target marks 28, 30, 32 on the left-hand and right-hand side thereof, said side target marks being arranged between the two adjustable limbs and the traverse 20. As shown in FIG. 2, the side target mark 28 of the measurement bracket is positioned in a recessed manner in the x-direction of the coordinate system 33 in relation to the side target marks 30, 32.

For the purposes of determining fitting parameters, a portion of the spectacle frame 16 worn by a subject is acquired digitally in the system 10. To this end, the system 10 has a tablet computer 34 which contains a camera 36. The tablet computer 34 has a touch-sensitive image screen 38. The camera 36 has imaging optics 38 and contains an image sensor 40 which is arranged in a camera image plane 42.

The tablet computer 34 contains an inclination sensor 44, by means of which the angle $\gamma$ of the inclination of the camera image plane 42 in relation to the direction 46 of gravity can be detected. The inclination sensor 44 renders it possible to detect the inclination of the camera image plane 42 in relation to the direction 46 of gravity, i.e. about a horizontal axis 43 parallel to the camera image plane 42, when the camera 36 is used to record an image of the spectacle frame 16 worn by a subject in the portion of the spectacle frame 16 worn by a subject. The tablet computer 34 contains an application program (app) for the purposes of acquiring images with the associated angle γ of the inclination of the camera image plane 42.

The system 10 has a computer unit 48 embodied as a server computer. The computer unit 48 is wirelessly connected to the tablet computer 34 by means of WLAN transfer technology. For an image recorded with the camera 36 in the tablet computer 34, the computer unit 48 obtains the digital image data acquired by means of the image sensor 40 and the angle γ of the inclination of the camera image plane 42 in relation to the direction 46 of gravity.

The computer unit 48 contains a computer program which, in a computational algorithm, establishes the pantoscopic angle α, related to the direction 46 of gravity, of the spectacle frame 16 and the head rotation angle β in relation to the optical axis 50 of the camera 36 by digital image analysis, i.e. by image evaluation, from an image of the portion of the spectacle frame 16 worn by the subject with the measurement bracket 18 connected thereto, said measurement bracket containing the three front target marks 22, 24, 26 arranged at the traverse 20 thereof. Thus, the head rotation angle β is that angle which the optical axis 50 of the camera 36 forms with a plane 52 which is perpendicular to the distance line 54 of the pupils 56, 58 of the eyes 60, 62 of the subject, that is, to an imaginary connecting line between the eyes 60, 62 of the subject.

Here, the pantoscopic angle α of the spectacle frame 16 and the head rotation angle β are calculated from the position of the front target marks 22, 24, 26 in the image plane 42 of the camera 36. What is employed here is the fact that the central front target mark 24 has the distance B from the plane in which the front target marks 22 and 26 of the measurement bracket 18 lie, as shown in FIG. 3A and FIG. 3B.

If the spectacle frame 16 with the measurement bracket 18 has a pantoscopic angle α=0° in relation to the vertical direction and if γ=0 likewise applies to the inclination angle γ of the image plane 42 of the camera 36 in relation to the vertical direction, then what this achieves is that the camera 36 acquires the front target marks 22, 24, 26 as an image in which said marks lie on an imagined connecting line 66, as emerges from FIG. 3A. However, if the spectacle frame 16 is inclined in relation to the vertical direction, as shown in FIG. 4B, the image of the central front target mark 24 acquired by means of the camera 36 in the image plane 42 of the camera 36 is offset by a value A in relation to an imaginary connecting line 66 between the image of the front target mark 22 and the image of the front target mark 26, like FIG. 4A. Therefore, the sought-after pantoscopic angle a can be established as α=arctan(A/B) from the known distance B of the front target mark 24 from the connecting line of the front target marks 22, 26.

If the image plane 42 of the camera 36 is inclined by a horizontal axis, parallel to the image plane 42, corresponding to the angle γ, the computer program still corrects the pantoscopic angle α, established on the basis of the relationship described above, by the angle γ detected by means of the inclination sensor 44.

If the optical axis 50 of the camera 36 includes the head rotation angle β>0 with the plane 52, the image, detected by means of the camera 36, of the central front target mark 24 in the image plane 42 of the camera 36 is likewise displaced, in respect of the view of FIG. 3A, by a value C between the image of the front target mark 22 and the image of the front target mark 26, as can be seen in FIG. 5A and FIG. 5B. Here, β=arctan(C/B) applies for the head rotation angle β.

From the relative position, established by means of image evaluation, of the front target marks 22, 24 and 26 in the image plane 42 of the camera 36, the computer program in the computer unit 48 then calculates the head rotation angle β on the basis thereof.

If the image plane 42 of the camera 36 is inclined by a horizontal axis, parallel to the image plane 42, corresponding to the angle β, the computer program, in the process, still corrects the head rotation angle β established on the basis of the relationship described above in accordance with the angle λ detected by means of the inclination sensor 44 to form a corrected head rotation angle, which corresponds to a horizontal alignment of the optical axis 50 of the camera.

Then, the computer program is used to convert image of the portion of the spectacle frame 16 worn by the subject with the measurement bracket 18 connected thereto, said measurement bracket containing the three front target marks 22, 24, 26 arranged on the traverse 20 thereof, into an image data record which is corrected in accordance with the inclination of the image plane 42 of the camera 36 about the horizontal axis 43 and the corrected head rotation angle corresponding to a horizontal alignment of the optical axis 50 of the camera such that this image data record then corresponds to a camera image in which the subject looks into the camera 36 and the image plane 42 of the camera 36 is aligned precisely vertically.

In respect to the position of the tablet computer 34 and the direction of the optical axis 50 of the imaging optics 38 of the camera 36, the user of the system 10 is virtually non-restricted when acquiring images of the portion of the spectacle frame 16, worn by the subject, with a measurement bracket 18 assembled on the spectacle frame 16. In particular, the inventors could show that the accuracy for the detection of spectacle lens fitting parameters in the system 10 is not impaired, even if the following applies to the inclination angle γ of the image plane 42 of the camera 36 in the tablet computer 34: $-20°≤γ≤20°$.

Figure 6:
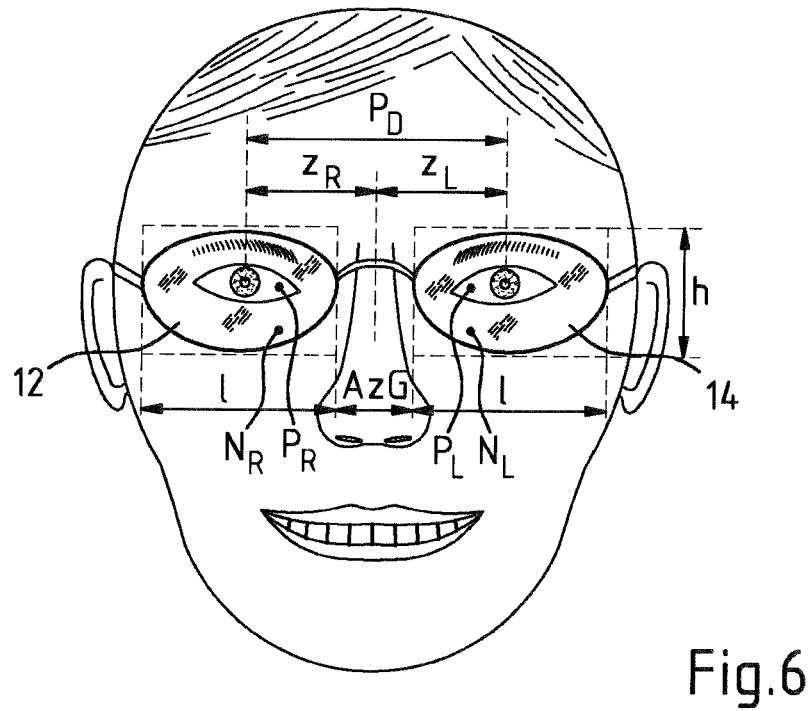
FIG. 6 shows a top view of a spectacle frame.
Figure 7:
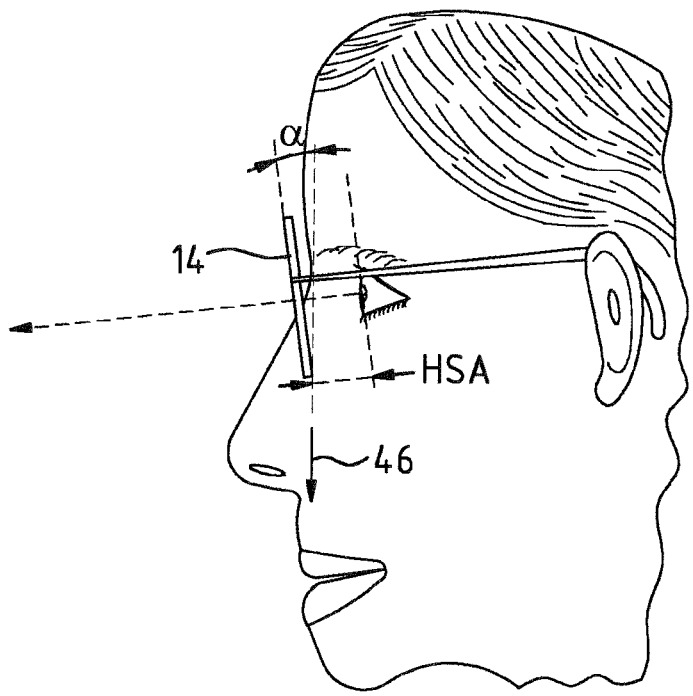
FIG. 7 shows a side view of a spectacle frame.

FIGS. 5A and 5B are a plan view of the frame plane and show, therein, different fitting parameters for spectacle lenses in a spectacle frame. FIG. 6 shows a side view of a spectacle frame with the eye of the subject.

In the system 10, the visual points for distance can also be determined as fitting parameters, taking into account the inclination angle γ. It is possible to determine the distance visual point $P_{R/L}$ (right/left centration point) from the point through which the subject looks at the camera in an acquired image. It is likewise possible to determine a near visual point $N_{R/L}$ (right/left near visual point) which, together with the distance visual point $P_{R/L}$, defines a progressive lens. In addition to the near visual points $N_{R/L}$, it is also possible to determine the angle ε between the viewing direction of the eye of a subject when looking into the distance and the viewing direction when looking close-by, for example, when reading. The system 10 does not require a reading situation to be acquired by a further camera or together with a further camera and subsequently be evaluated.

The computational algorithm of the computer program in the computer unit 48 of the system 10 is configured in such a way that, using it, it is not only possible to determine the pantoscopic angle a of the spectacle frame (pantoscopic tilt), but, alternatively or additionally, also the frame dimensions (l, h, AzG [distance between lenses]), the interpupillary distance (PD, $z_R$, $z_L$), the centration distance ($x_R$, $y_R$, $X_L$, $y_L$), the vertex distance (HAS), the face form angle and the required lens blank diameter.

In summary, the following preferred features of the invention, in particular, should be registered: In a method for determining at least one fitting parameter for a spectacle lens received in a spectacle frame 16, an image, lying in an image plane, of at least one portion of the spectacle frame 16 worn by a subject is acquired. In so doing, the inclination of the image plane 42 about a horizontal axis 43 which is parallel to the image plane 42 is established when acquiring the image and, in the process, the at least one fitting parameter is established from the acquired image of the portion of the subject with the spectacle frame 16 worn by the subject and the established inclination of the image.

It is understood that the foregoing description is that of the preferred embodiments of the invention and that various changes and modifications may be made thereto without departing from the spirit and scope of the invention as defined in the appended claims.

REFERENCE NUMERALS

10 System
12, 14 Spectacle lens
16 Spectacle frame
18 Measurement bracket
19 Front side
20 Traverse
22, 24, 26 Front target marks
28, 30, 32 Lateral target marks
33 Coordinate system
34 Tablet computer
36 Camera
38 Imaging optics/image screen
40 Image sensor
42 Image plane
43 Horizontal axis
44 Inclination sensor
46 Direction
48 Computer unit
50 Optical axis
52 Plane
54 Distance line
56, 58 Pupils
60, 62 Eyes
66 Connecting line

What is claimed is:

1. A method for determining an adaptive parameter for a spectacle lens accommodated in a spectacle frame with a system including a processor, program code stored on a non-transitory computer readable medium configured to perform method steps when executed by the processor, the system further including an inclination sensor, a handheld camera defining an optical axis and at least three front target marks spatially fixed relative to said spectacle frame and arranged on a measurement bracket defining a front side with a first one of said front target marks being spatially offset perpendicularly to said front side with respect to the second and third ones of said front target marks, the method comprising the steps of:
with said handheld camera, capturing an image lying in an image plane of a section of said spectacle frame worn by a patient together with said three front target marks with the patient assuming a pose wherein the patient need not look into the camera;
determining an inclination angle ($\gamma$) of said image plane about a horizontal axis parallel to said image plane via said inclination sensor;
determining the position of said front target marks in the captured image utilizing image analysis performed by said program code when executed by the processor;
determining a forward inclination angle of said spectacle frame from said position of said front target marks determined from said image analysis;
correcting said forward inclination angle to a corrected forward inclination angle ($\alpha$) in relation to a vertical direction in correspondence to said determined inclination angle ($\gamma$) of said image plane;
determining a head rotation angle ($\beta$) of the head of said patient with respect to said optical axis of said handheld camera with said head rotation angle ($\beta$) being conjointly defined by said optical axis and a plane running perpendicularly to a distance line between the pupils of the eyes of said patient;
correcting said head rotation angle ($\beta$) to a corrected head rotation angle corrected in correspondence to a horizontal alignment of said optical axis of said handheld camera; and,
determining at least one adaptive parameter for fitting the spectacle lens in the spectacle frame so as to cause an optical center of the spectacle lens to coincide with a visual axis of an eye of the patient from the captured image of the section of the spectacle frame worn by said patient and said corrected forward inclination angle ($\alpha$) as well as said corrected head rotation angle via image analysis performed by said program code when executed by the processor.

2. The method of claim 1, wherein said image is captured with a digital camera incorporating an inclination sensor capturing the inclination of said image plane about a horizontal axis.

3. The method of claim 1, comprising the further step of: capturing said section of said spectacle frame worn by the patient when said measurement bracket is connected to said spectacle frame wherein said front side of said measurement bracket accommodates said three front target marks for a measurement of said forward inclination angle ($\alpha$) of said spectacle frame to be measured wherein said first front target mark is arranged spatially offset perpendicular to said forward side of said measurement bracket relative to said second and third front target mark.

4. The method of claim 1, wherein said adaptive parameter is selected from the group comprising frame measure (l, h, AzG), pupillary distances (PD, $z_R$, $z_L$), centerpoint spacing ($x_R$, $y_R$, $x_L$, $y_L$), cornea vertex spacing (HSA), frame forward inclination, frame disc angle and required raw glass diameter.

5. A system for determining an adaptive parameter for a spectacle lens accommodated in a spectacle frame, the system comprising:
a handheld camera having an image plane and defining an optical axis;
an inclination sensor detecting the inclination of said image plane of said handheld camera about a horizontal axis;
at least three front target marks spatially fixed relative to said spectacle frame and arranged on a measurement bracket defining a front side with a first one of said front target marks being spatially offset perpendicularly to said front side with respect to the second and third ones of said front target marks;
a computer unit including a computer readable storage medium and a computer program for determining said adaptive parameter from an image of a section of said spectacle frame worn by a patient and the determined inclination of said image stored on said computer readable storage medium, wherein said image is captured by said handheld camera; and, said computer unit being configured to determine said adaptive parameter in accordance with a method including the steps of:

with said handheld camera, capturing an image lying in an image plane of a section of said spectacle frame worn by a patient together with said three front target marks with the patient assuming a pose wherein the patient need not look into the camera;

determining an inclination angle ($\gamma$) of said image plane about a horizontal axis parallel to said image plane;

determining the position of said front target marks in the captured image utilizing image analysis performed by said program code when executed by a processor of said computer unit;

determining a forward inclination angle of said spectacle frame from said position of said front target marks determined from said image analysis;

correcting said forward inclination angle to a corrected forward inclination angle ($\alpha$) in correspondence to said determined inclination angle ($\gamma$) of said image plane;

determining a head rotation angle ($\beta$) of the head of said patient with respect to said optical axis of said handheld camera with said head rotation angle ($\beta$) being conjointly defined by said optical axis and a plane running perpendicularly to a distance line between the pupils of the eyes of said patient;

correcting said head rotation angle ($\beta$) to a corrected head rotation angle corrected in correspondence to a horizontal alignment of said optical axis of said handheld camera; and, with image analysis, determining at least one adaptive parameter from the captured image of the section of the spectacle frame worn by said patient and said corrected forward inclination angle ($\alpha$) as well as said corrected head rotation angle.

6. The system of claim 5, wherein said handheld camera is integrated into a tablet computer and/or is integrated into a mobile telephone and said computer unit is configured as a server connected to said tablet computer and/or said mobile telephone.

7. The system of claim 6, wherein said tablet computer and/or said mobile telephone communicate wirelessly with said server.

8. A computer program having a program code stored on a non-transitory computer-readable medium, the program code being for determining an adaptative parameter for a spectacle lens accommodated in a spectacle frame, the adaptive parameter being determined with a system including a handheld camera having an image plane and defining an optical axis, the system further including at least three front target marks spatially fixed relative to said spectacle frame and arranged on a measurement bracket defining a front side with a first one of said front target marks being spatially offset perpendicularly to said front side with respect to the second and third ones of said front target marks, wherein the handheld camera is configured to capture an image lying in an image plane of a section of said spectacle frame worn by a patient together with said three front target marks with the patient assuming a pose wherein the patient need not look into the camera, the system further including an inclination sensor configured to detect the inclination of said image plane of said camera about a horizontal axis, the system further including a computer unit having a processor, said program code being configured, when executed by the processor, to:

determine an inclination angle ($\gamma$) of said image plane about a horizontal axis parallel to said image plane via said inclination sensor;

determine the position of said front target marks in the captured image utilizing image analysis;

determine a forward inclination angle of said spectacle frame from said position of said front target marks determined from said image analysis;

correct said forward inclination angle to a corrected forward inclination angle ($\alpha$) in correspondence to said determined inclination angle ($\gamma$) of said image plane;

determine a head rotation angle ($\beta$) of the head of said patient with respect to said optical axis of said handheld camera with said head rotation angle ($\beta$) being conjointly defined by said optical axis and a plane running perpendicularly to a distance line between the pupils of the eyes of said patient;

correct said head rotation angle ($\beta$) to a corrected head rotation angle corrected in correspondence to a horizontal alignment of said optical axis of said handheld camera; and, with image analysis, determine at least one adaptive parameter from the captured image of the section of the spectacle frame worn by said patient and said corrected forward inclination angle ($\alpha$) as well as said corrected head rotation angle.

9. A method for determining an adaptive parameter for a spectacle lens accommodated in a spectacle frame with a system including a processor, program code stored on a non-transitory computer readable medium configured to perform method steps when executed by the processor, the system further including an inclination sensor, a camera defining an optical axis and at least three front target marks spatially fixed relative to said spectacle frame and arranged on a measurement bracket defining a front side with a first one of said front target marks being spatially offset perpendicularly to said front side with respect to the second and third ones of said front target marks, the method comprising the steps of:

with said camera, capturing an image lying in an image plane of a section of said spectacle frame worn by a patient together with said three front target marks with the patient assuming a pose wherein the patient need not look into the camera;

determining an inclination angle ($\gamma$) of said image plane about a horizontal axis parallel to said image plane via said inclination sensor;

determining the position of said front target marks in the captured image utilizing image analysis performed by said program code when executed by the processor;

determining a forward inclination angle of said spectacle frame from said position of said front target marks determined from said image analysis;

correcting said forward inclination angle to a corrected forward inclination angle ($\alpha$) in relation to a vertical direction in correspondence to said determined inclination angle ($\gamma$) of said image plane;

determining a head rotation angle ($\beta$) of the head of said patient with respect to said optical axis of said camera with said head rotation angle ($\beta$) being conjointly defined by said optical axis and a plane running perpendicularly to a distance line between the pupils of the eyes of said patient;

correcting said head rotation angle ($\beta$) to a corrected head rotation angle corrected in correspondence to a horizontal alignment of said optical axis of said camera; and, determining at least one adaptive parameter for fitting the spectacle lens in the spectacle frame so as to cause an optical center of the spectacle lens to coincide with a visual axis of an eye of the patient from the captured image of the section of the spectacle frame worn by said patient and said corrected forward inclination angle ($\alpha$) as well as said corrected head rotation angle via image analysis performed by said program code when executed by the processor.

10. A system for determining an adaptive parameter for a spectacle lens accommodated in a spectacle frame, the system comprising:
- a camera having an image plane and defining an optical axis;
- an inclination sensor detecting the inclination of said image plane of said camera about a horizontal axis;
- at least three front target marks spatially fixed relative to said spectacle frame and arranged on a measurement bracket defining a front side with a first one of said front target marks being spatially offset perpendicularly to said front side with respect to the second and third ones of said front target marks;
- a computer unit including a computer readable storage medium and a computer program for determining said adaptive parameter from an image of a section of said spectacle frame worn by a patient and the determined inclination of said image stored on said computer readable storage medium, wherein said image is captured by said camera; and,
- said computer unit being configured to determine said adaptive parameter in accordance with a method including the steps of:
- with said camera, capturing an image lying in an image plane of a section of said spectacle frame worn by a patient together with said three front target marks with the patient assuming a pose wherein the patient need not look into the camera;
- determining an inclination angle ($\gamma$) of said image plane about a horizontal axis parallel to said image plane;
- determining the position of said front target marks in the captured image utilizing image analysis performed by said program code when executed by a processor of said computer unit;
- determining a forward inclination angle of said spectacle frame from said position of said front target marks determined from said image analysis;
- correcting said forward inclination angle to a corrected forward inclination angle ($\alpha$) in correspondence to said determined inclination angle ($\gamma$) of said image plane;
- determining a head rotation angle ($\beta$) of the head of said patient with respect to said optical axis of said camera with said head rotation angle ($\beta$) being conjointly defined by said optical axis and a plane running perpendicularly to a distance line between the pupils of the eyes of said patient;
- correcting said head rotation angle ($\beta$) to a corrected head rotation angle corrected in correspondence to a horizontal alignment of said optical axis of said camera; and,
- with image analysis, determining at least one adaptive parameter from the captured image of the section of the spectacle frame worn by said patient and said corrected forward inclination angle ($\alpha$) as well as said corrected head rotation angle.

11. A computer program having a program code stored on a non-transitory computer-readable medium, the program code being for determining an adaptative parameter for a spectacle lens accommodated in a spectacle frame, the adaptive parameter being determined with a system including a camera having an image plane and defining an optical axis, the system further including at least three front target marks spatially fixed relative to said spectacle frame and arranged on a measurement bracket defining a front side with a first one of said front target marks being spatially offset perpendicularly to said front side with respect to the second and third ones of said front target marks, wherein the camera is configured to capture an image lying in an image plane of a section of said spectacle frame worn by a patient together with said three front target marks with the patient assuming a pose wherein the patient need not look into the camera, the system further including an inclination sensor configured to detect the inclination of said image plane of said camera about a horizontal axis, the system further including a computer unit having a processor, said program code being configured, when executed by the processor, to:
- determine an inclination angle ($\gamma$) of said image plane about a horizontal axis parallel to said image plane via said inclination sensor;
- determine the position of said front target marks in the captured image utilizing image analysis;
- determine a forward inclination angle of said spectacle frame from said position of said front target marks determined from said image analysis;
- correct said forward inclination angle to a corrected forward inclination angle ($\alpha$) in correspondence to said determined inclination angle ($\gamma$) of said image plane;
- determine a head rotation angle ($\beta$) of the head of said patient with respect to said optical axis of said camera with said head rotation angle ($\beta$) being conjointly defined by said optical axis and a plane running perpendicularly to a distance line between the pupils of the eyes of said patient;
- correct said head rotation angle ($\beta$) to a corrected head rotation angle corrected in correspondence to a horizontal alignment of said optical axis of said camera; and,
- with image analysis, determine at least one adaptive parameter from the captured image of the section of the spectacle frame worn by said patient and said corrected forward inclination angle ($\alpha$) as well as said corrected head rotation angle.

* * * * *

UNITED STATES PATENT AND TRADEMARK OFFICE
CERTIFICATE OF CORRECTION

Page 1 of 1

PATENT NO. : 10,890,786 B2
APPLICATION NO. : 15/212060
DATED : January 12, 2021
INVENTOR(S) : J. Cabeza-Guillen et al.

It is certified that error appears in the above-identified patent and that said Letters Patent is hereby corrected as shown below:

In the Specification

In Column 5:
Line 48: delete "angle a" and substitute -- angle α -- therefor.

In Column 6:
Line 58: delete "angle a" and substitute -- angle α -- therefor.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*